(12) United States Patent
Doskocil et al.

(10) Patent No.: US 11,638,814 B2
(45) Date of Patent: May 2, 2023

(54) METHOD FOR NEUROMODULATION TREATMENT OF NEURODEGENERATIVE DISEASE

(71) Applicant: TESLA MEDICAL S.R.O., Ostrava (CZ)

(72) Inventors: Lukas Doskocil, Chocen (CZ); Jan Krhut, Ostrava-Zabreh (CZ); Lukas Peter, Ostrava-Poruba (CZ); Michal Drahos, Hlinsko v Cechach (CZ); Zdenek Krcil, Pardubice (CZ)

(73) Assignee: TESLA MEDICAL S.R.O., Ostrava (CZ)

( * ) Notice: Subject to any disclaimer, the term of this patent is extended or adjusted under 35 U.S.C. 154(b) by 0 days.

(21) Appl. No.: 17/724,821

(22) Filed: Apr. 20, 2022

(65) Prior Publication Data

US 2022/0241583 A1  Aug. 4, 2022

Related U.S. Application Data

(63) Continuation-in-part of application No. 16/339,790, filed as application No. PCT/CZ2016/000113 on Oct. 5, 2016, now Pat. No. 11,420,052.

(51) Int. Cl.
*A61N 1/04* (2006.01)
*A61N 1/36* (2006.01)
*A61N 1/02* (2006.01)

(52) U.S. Cl.
CPC .......... *A61N 1/0456* (2013.01); *A61N 1/025* (2013.01); *A61N 1/3603* (2017.08);
(Continued)

(58) Field of Classification Search
CPC .. A61N 1/0456; A61N 1/025; A61N 1/36025; A61N 1/3603; A61N 1/36067; A61N 1/36003; A61N 1/36082
See application file for complete search history.

(56) References Cited

U.S. PATENT DOCUMENTS 5,800,470 A  9/1998  Stein et al.
5,814,093 A  9/1998  Stein
(Continued)

FOREIGN PATENT DOCUMENTS

JP  2016515463 A  5/2016
JP  2016515869 A  6/2016
(Continued)

OTHER PUBLICATIONS

International Search Report related to Application No. PCT/CZ2016/000113; dated Aug. 8, 2017.
(Continued)

*Primary Examiner* — Mark W. Bockelman
(74) *Attorney, Agent, or Firm* — von Briesen & Roper, s.c.

(57) ABSTRACT

The present disclosure provides a neuromodulation method for treating neurodegenerative disease. The neuromodulation method comprises attaching a first active electrode to a patient's leg in the back of the knee area in an expected location of a peroneal nerve of the first leg and attaching a grounding electrode to the patient's body. Generating electrical pulses by a pulse generator connected to the first active electrode and the grounding electrode. Stimulating by the first active electrodes the peroneal nerve of the first leg and controlling via a control unit a flow of the generated pulses to the first electrode.

18 Claims, 5 Drawing Sheets

(52) U.S. Cl.
CPC ..... *A61N 1/36025* (2013.01); *A61N 1/36067* (2013.01); *A61N 1/36082* (2013.01)

(56) References Cited

U.S. PATENT DOCUMENTS

| | | |
|---|---|---|
| 7,257,448 B2 | 8/2007 | Crowe et al. |
| 8,660,646 B2 | 2/2014 | Laing et al. |
| 9,138,579 B2 | 9/2015 | Wolpaw et al. |
| 2009/0306531 A1 | 12/2009 | Leuthardt et al. |
| 2011/0137375 A1 | 6/2011 | McBride |
| 2013/0268023 A1 | 10/2013 | Jahns |
| 2014/0046423 A1* | 2/2014 | Rajguru ............... A61N 2/02 607/144 |
| 2014/0303460 A1* | 10/2014 | Corley ............... A61B 5/1072 600/301 |
| 2014/0379045 A1 | 12/2014 | Rahimi et al. |
| 2015/0126894 A1 | 5/2015 | Benson et al. |
| 2015/0324549 A1 | 11/2015 | Nearhood et al. |
| 2016/0121109 A1 | 5/2016 | Edgerton et al. |
| 2021/0236328 A1 | 8/2021 | Popielarski et al. |

FOREIGN PATENT DOCUMENTS

| | | |
|---|---|---|
| WO | 2005023087 A2 | 3/2005 |
| WO | 2008062395 A1 | 5/2008 |
| WO | 2012106548 A2 | 8/2012 |
| WO | 2013113297 A1 | 8/2013 |
| WO | 2014113813 A1 | 7/2014 |
| WO | 2015066597 A2 | 5/2015 |

OTHER PUBLICATIONS

Japanese Notice of Reasons for Refusal related to Application No. 2019-519321; dated Jul. 14, 2020.
Japanese Search Report by Registered Search Organization; dated Jul. 6, 2020.

* cited by examiner

SPM{T$_{21}$}

METHOD FOR NEUROMODULATION TREATMENT OF NEURODEGENERATIVE DISEASE

CROSS-REFERENCE TO RELATED APPLICATION

This Application is a continuation-in-part patent application under 35 USC § 121 claiming priority to U.S. non-provisional patent application Ser. No. 16/339,790 filed on Apr. 5, 2019 which was a U.S. national phase filing under 35 USC § 371 of International Patent Application No. PCT/CZ2016/000113 filed on Oct. 5, 2016.

FIELD OF THE TECHNICAL DISCLOSURE

Technical Field

The present disclosure relates to a medical method for a neuromodulation treatment of a patient.

Background of the Disclosure

Use of an electrical stimulation of neurons for the benefit of a human subject is described to treat incontinence, to stimulate muscles for the purpose of simulating exercise and subsequent increase of heart rate, to improve lymphatic drainage of the lower limbs, to stimulate neurons, and for other related applications associated with the positive effects of applied electric current to human body.

For instance, a percutaneous tibial nerve stimulation (PTNS) method for treating incontinence uses a needle introduced in close proximity of the nerve in the ankle region, and by means of an electric current connected thereto, it stimulates the nerve as well as the adjacent nerves in the pelvic area. Such repeated stimulation of the pelvic region can have a significantly positive effect on both the functioning of muscles and the communication between the patient's body and nervous system. Improvement of a bladder function by a nerve stimulation using an electrical current delivered to the proximity of the nerve via a body invasive needle may be achieved by repeated sessions each lasting several minutes. The historic disadvantages of inserting needles into the patient's body include mainly pain, the risk of infection and nerve damage, and also a requirement of a medical professional to carry out the treatment. Additionally, for a successful treatment, it is important to ensure an accurate targeting of the nerve to be stimulated. In practice, the subjective feeling of the patient is used. However, this is not always accurate, and it has proven to be the biggest obstacle in impacting success rates of the treatment.

Whilst the use of a neuromodulation technology is known for an incontinence treatment an effective neuromodulation method and a device for a treatment of variety of neurodegenerative diseases is still left to be invented.

SUMMARY OF THE DISCLOSURE

One objective of the present disclosure is to remedy the drawback and provide an effective neuromodulation method and a device for a treatment of variety of neurodegenerative diseases.

An aspect of the present disclosure provides a device for stimulating the peripheral nerves, comprising a memory unit, at least one electrode attached to the patient's body for generating pulses, a control unit connected to the electrode for setting at least one electrode pulse parameter, and further connected to at least one response detector to neuromodulation. The response detector to neuromodulation is connected to a control unit for transmitting information on the frequency of movement of at least a part of the patient's body. The control unit of the device further sets the flow of current of electrode pulses automatically, depending on information about the frequency value of movement of at least a part of the patient's body.

The control unit receives information on the frequency value from the response detector to neuromodulation, or from memory. The detector of the device can be an optical sensor, an infrared sensor, an accelerometer, or a capacitive, inductive, thermal, flow, ultrasound, or magnetic sensor. In an alternative embodiment of the present disclosure, an electromyograph can also be used as a detector. In a preferred configuration, the detector can make use of more than one sensor.

The memory device can be at least one of the following: an HDD disk, SSD disc, flash memory, memory card, RAM, CD, DVD, or Blu-ray. In alternative configurations, the memory can be a remote storage device accessible through a network service.

Alternatively, the remote memory storage unit can be accessible through another neuromodulation device connected to the network service.

The control unit may change the frequency of the electrode pulses until it substantially equals the frequency of the recorded movements. The control unit may also change the flow of the current of pulses until the optimum frequency of recorded movement is reached.

The device can include one or more control units, which are separated. The control unit can be a part of the controller, which may further comprise a display device and user input for the operator. The control unit, according to the present disclosure, sets the frequency of the pulses in a range between 0.1 and 100 Hz and sets the length of the pulses in a range between 0.1 and 10 ms. The control unit, as per the present disclosure, may further set the shape of the pulse. The control unit of the present device may further set the polarity of the voltage ranging from positive to negative.

The control unit may communicate with a database stored in the memory, which is the internal memory of the control unit, or in a remote storage unit, available via network services. Here it may store the information on recommended parameters of the flow of the current of pulses. The database may further include the patient's personal data, such as but not limited to: information on the patient's age, sex, information on identity and personal data of the patient, for example identification number, number of the insurance, address, social security number, credit card number and so on. As per the present disclosure, the control unit may send the information from the database to the remote storage. As per the present disclosure, the detector and the controller may be parts of a single construction. In one aspect, the controller and at least one of the electrodes may be parts of a single unit. Such single unit can be a device electrically and mechanically connected. In some aspects, a single unit may be also integrated in a single construction.

A further aspect of the present disclosure provides a method for a neuromodulation treatment of a low urinary tract dysfunction that may include treatment of symptoms of an overactive bladder and/or fecal incontinence in humans. The inventors surprisingly found the above defined method may be also applicable for a neuromodulation treatment of the neurodegenerative diseases such as Parkinson's, Alzheimer's and potentially also Huntington's disease, Amyotrophic lateral sclerosis (ALS), Motor neuron disease and other neurodegenerative diseases.

Particularly, the method involves a control unit and a one active electrode or at least two active electrodes capable of generating electrical pulses. The at least two active electrodes are attached to the patient's body, so that a first active electrode of the at least two active electrodes is attached to either of the patient's legs and a second active electrode of the at to least two active electrodes is also attached to either of the patient's legs. The first active electrode of the at least two active electrodes may be attached to a first patient's leg in the back of the knee area in an expected location of a peroneal nerve of the first leg. The second active electrode of the at least two active electrodes may be attached to a second patient's leg in the back of the knee area in an expected location of a peroneal nerve of the second leg.

Alternatively, the first active electrode may be attached to the first leg of the patient and the second active electrode is also attached to the same leg. The first active electrode may be attached to the back of either knee and the second active electrode is attached to the back of the other knee.

After the active electrodes are attached, the first electrical pulses in the first active electrode may be delivered to the patient's body, and at the same time or subsequently, other electrical pulses in the second active electrode may be delivered to the patient's body. In the following step, the flow of the pulse current may be set. The preferred method further involves a step of synchronizing the timing of each pulse.

In one aspect the active electrodes are attached in the proximity of branches of a peripheral nerve.

The active electrodes may be attached to the patient so that the first active electrode may be attached to the first branch of the sciatic nerve and another, second, active electrode may be attached to another branch of the sciatic nerve. Preferably, one of the following nerves is stimulated: the lumbosacral plexus, sciatic nerve, common peroneal nerve, tibial nerve, pudendal nerve, superior gluteal nerve, inferior gluteal nerve, posterior cutaneous femoral nerve, obturator internus nerve, piriformis, quadratus femoris nerve, plantar nerve, coccygeal nerve. In preferred embodiment, pudendal nerve or tibial nerve or common peroneal.

In one aspect, the first active electrode may be attached to one leg of the patient and the second active electrode may be attached to the other leg of the patient. In another aspect of to the present method, the first active electrode may be attached to the first leg of the patient and the second active electrode is also attached to the same leg of the patient.

The active electrodes are, according to the present disclosure, transcutaneous, percutaneous or electrodes for long term implantation. In one aspect of the present method, the first active electrode may be attached to the back of either knee and the second active electrode may be attached to the back of the other knee. Synchronization of the electrical pulses delivered to patient via the first and the second active electrodes may be achieved by timing the pulses to beginning of each pulse. The timing of pulses may be synchronized per the time of delivery of the pulse from the first active electrode and the time of delivery of the pulse from the other active electrode into the target area. The target area may be a sacral plexus or a sciatic nerve. The method, further involves placing a grounding electrode onto the patient's body, most advantageously on the patient's suprapubic, hypogastric or sacral area.

The electrical pulses may have, a frequency between 0.1 Hz and 100 Hz, a pulse width between 0.1 ms and 5 ms, a current between 0 mA and 250 mA and a voltage between 0 V and 90 V. The frequency of the electrical pulses may be set between 2.5 Hz and 60 Hz and the pulse width of electrical pulses may be between 0.1 ms and 2.5 ms. Each of the active may have an active surface greater than 0.3100 square inch (2 cm$^2$), the electrical pulses may have have a current between 15 mA and 250 mA. Alternatively, each of the active electrodes may have an active surface between 0.0775 square inch (0.5 cm$^2$) and 0.3100 square inch (2 cm$^2$), the electrical pulses may have a current between 0 mA and 15 mA. Alternatively, each of the active electrodes may have an active surface less than 0.0775 square inch (0.5 cm$^2$), the electrical pulses may have a current between 0 mA and 5 mA.

The electrical pulses may have substantially a rectangular or right-triangular shape and are monophasic or biphasic. The time of the pulses may be determined by an algorithm stored in the control unit's memory.

The method may further include the following steps for a precise positioning of the first and second active electrode. After attachment of any of the active electrodes, the electric pulses are generated, and then reflex movements of at least one part of the patient's body may be monitored. The sufficiency of the reflex movements of the monitored part of patient's body may be determined. If the reflex movements of the monitored part of the patient's body are insufficient, the active electrode is repositioned. The steps may be repeated until the reflex movements of at least one part of the patient's body are sufficient and thus the optimal location is found for the active electrode. The method may further include collecting information about the use of the neuromodulation medical device as described above, other similar neuromodulation devices or other medical devices. The method may involves collecting information from the control unit. The information may be sent from the control unit to a memory. The information may be stored in a database. The information may be retrieved from said database. The medical device as describe above may be a therapeutic medical device, a surgical medical device or a diagnostic medical device. The control unit can communicate with the memory using any of the following means: GSM, Bluetooth, radio frequency, infrared communication, LAN, USB or a wireless internet connection. The method may further involve assigning an identification number to a patient, medical device or the information. The method may further involve steps of storing the information in the memory of the device and connecting the medical device to another medical device. The information may concern an undergone treatment and involve at least information on the pulse current flow, current intensity, the frequency of pulses. The method may further involve evaluating the information stored in the database and may use said information for invoicing. The method may further involve using the information stored in the database and send the information to the patient's physician and/or to the patient's electronic medical chart. The method may further involve using the information stored in the database to automatically alter the parameters of the treatment or use of the device.

BRIEF DESCRIPTION OF THE DRAWINGS

Other features and advantages of the invention appear from the following detailed to description of some of its embodiments, given by way of non-limiting example, and with reference to the accompanying drawings, in which.

DETAILED DESCRIPTION OF THE DISCLOSURE

Figure 1:
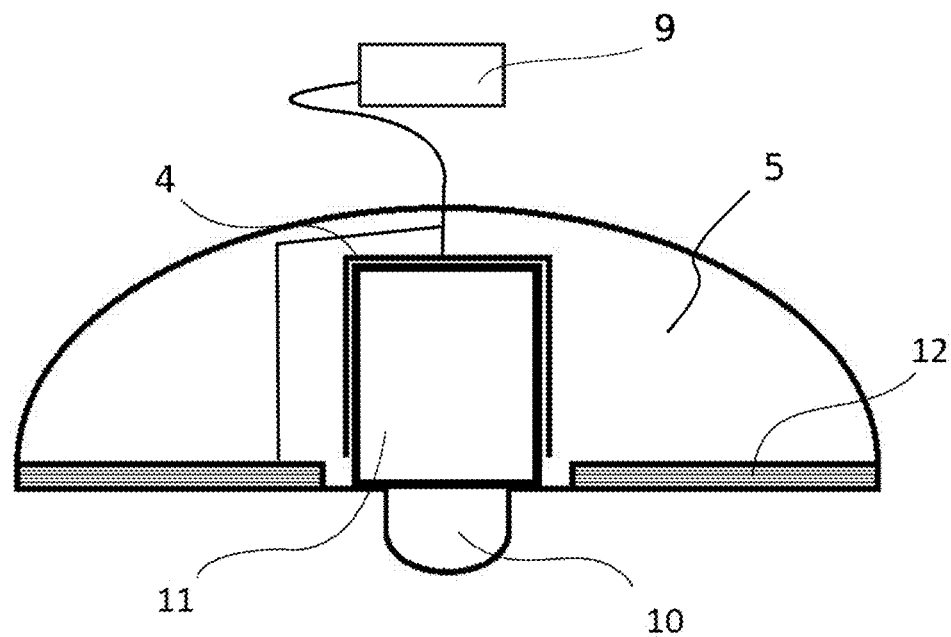
FIG. 1 shows a side view of the first embodiment of the electrode.

The foregoing summary, as well as the following detailed description of certain examples will be better understood when read in conjunction with the appended drawings. As used herein, an element or step recited in the singular and proceeded with the word "a" or "an" should be understood as not excluding plural of the elements or steps, unless such exclusion is explicitly stated. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

In the figures, the same references denote identical or similar elements, unless stated otherwise. In the drawings, the size of each element or a specific portion constituting the element is exaggerated, omitted, or schematically shown for convenience and clarity of description. Thus, the size of each component may not entirely reflect the actual size. In the case where it is judged that the detailed description of the related known functions or constructions may unnecessarily obscure the gist of the present disclosure, such explanation will be omitted.

Figure 4:
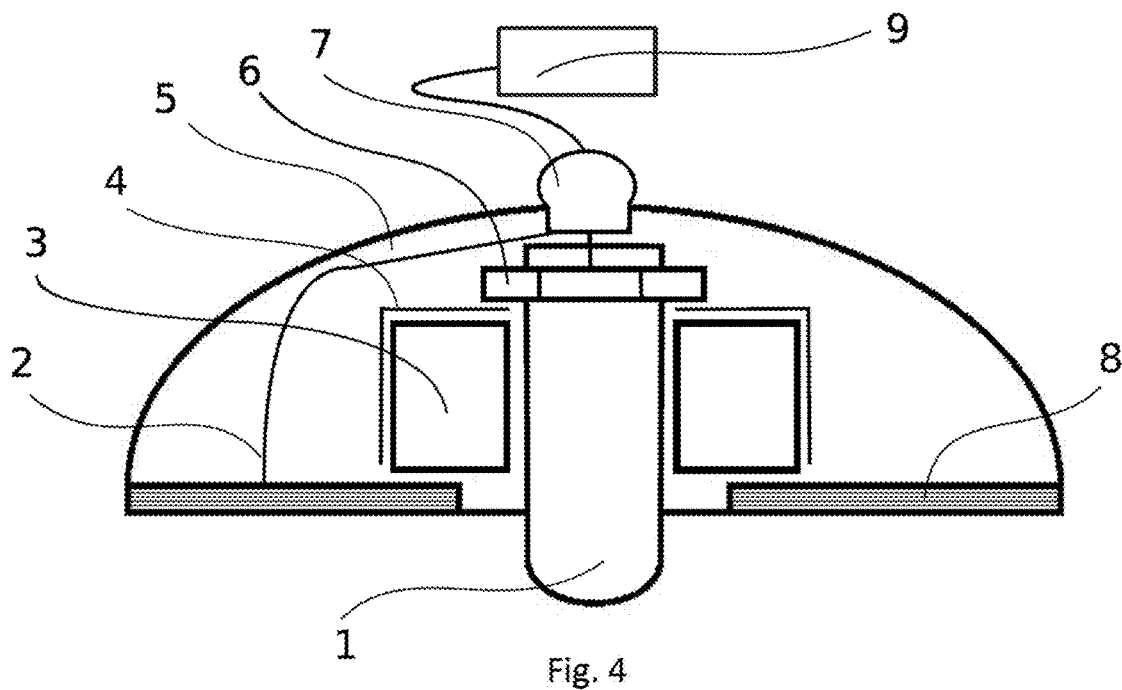
FIG. 4 shows a side of an alternative embodiment of the electrode.
Figure 5:
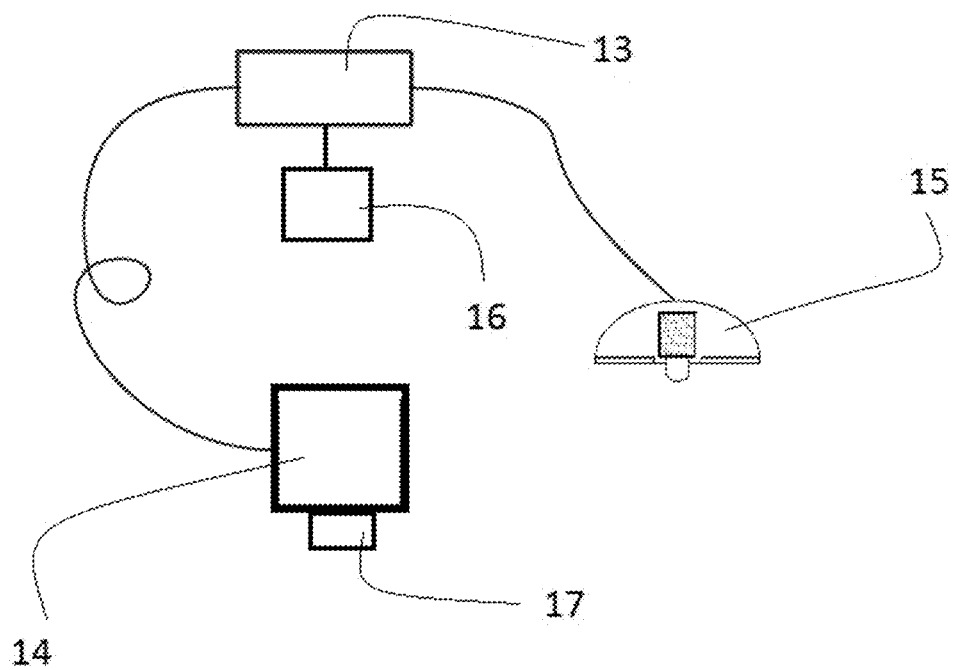
FIG. 5 shows whole device as per the present disclosure.

The present disclosure may include three major components, as shown in FIG. 5. The first component is a control unit 13, the second one is a detector 14, and the third is an electrode 15. The electrode can be of two types. The first possible embodiment of the electrode is the one shown in FIG. 4, which involves a magnet 3, a pole piece 4, the first pole 1 of the electrode and the second pole 8 of the electrode. The role of the magnet 3 is to increase the depth range at low stimulation currents. Together with the pole piece 4, it can linearize and concentrate parabolic electric field lines in an axial direction around the axis of the first pole 1 of the electrode. This substantially results in a tunnel effect for direction of movement and concentration of ions as carriers of electrical charges into the intercellular spaces. In this embodiment, the magnet 3 is permanent and has the shape of a hollow cylinder, with the first pole 1 of the electrode, for example of copper or brass, passing through its center. In the area of contact with the skin, the first pole 1 of the electrode is preferably round and coated with a layer of a suitable material, such as silver. The outer casing and the side of the permanent magnet 3 away from the skin are surrounded by the pole piece 4 of diamagnetic material. From the side away from the skin, the first pole 1 of the electrode is threaded for affixing a nut 6 and terminates with an adapter 7 for connecting the wire 2. Alternatively, the first pole 1 of the electrode is fixed in combination with a spring and the additional bottom part. The first pole 1 of the electrode is unthreaded and has a stop edge matching at least a part of the additional bottom part, wherein the first pole 1 of the electrode is fixed by a biasing spring member so that the spring member creates a tension between the first pole 1 of the electrode and, directly or indirectly, the fixing element 5. Thus force is applied in between the stop edge of the first pole 1 of the electrode and at least a part of the additional bottom part, resulting in fixing the first pole 1 of the electrode. The annulus-shaped second pole 8 of the electrode is secured to a fixing element 5 while separated from the first pole 1 of the electrode by a gap or another insulator. Thus, it is a bipolar electrode having the fixed position of the first pole 1 of the electrode and the second pole 8 of the electrode. The magnet 3 is separated from the first pole 1 of the electrode by an insulator and possibly also by an air gap. The magnet 3 is oriented with its north pole facing the tissue. The first pole 1 of the electrode, the magnet 3, the pole piece 4 and the second pole 8 of the electrode are made of materials intended for medical use, and are electrically insulated from each other, except for the area of the magnet 3 pole being in contact with the pole piece. Also, the insulation is of biocompatible material, which is also able to withstand frequent sterilization and is preferably also waterproof.

Preferably, the magnet 3 can be in the form of an electromagnet. Using a suitable source 9, as obvious to those skilled in the art, by means of a adjustable magnetic excitation, it is possible to set the shape of the area with the highest concentration of the charge carriers, i.e. a kind of a channel. Moreover, if several electromagnets are used, by means of their different excitations, it is possible to affect the direction of electric current flow to the tissue, i.e. direction of such a channel. As an example, this can be used for finding the desired nerve, even in the event of inaccurate placement of the electrostimulation device to the skin.

The DC source 9 is connected between the first pole 1 of the electrode and the second pole 8 of the electrode. The frequency can be set between 1 to 15 Hz and the pulses can be monophasic or biphasic, and for example, rectangular, sinusoidal or triangular, with exponential inclines or declines, and widths from 0.1 to 5 ms with a current range from 0 to 50 mA. A frequency from 2 to 6 Hz appears to be the most preferred and is very efficient.

Further included is a harness for fixing the device to a particular site and a power supply. Proper placement of electrostimulation electrodes is crucial for the efficiency of the entire method and for eliminating the risk of reduced efficiency of the method due to improper handling of the electrode. The role of the fixing element 5 is to ensure repeated attachment of the electrodes to the same electrostimulation site. To fix the position of the electrode, a special harness is used which can use the shape of a human body as a fixation point to create a shape that is permanently adapted to the patient and ensures equal conditions for each stimulation session.

Figure 2:
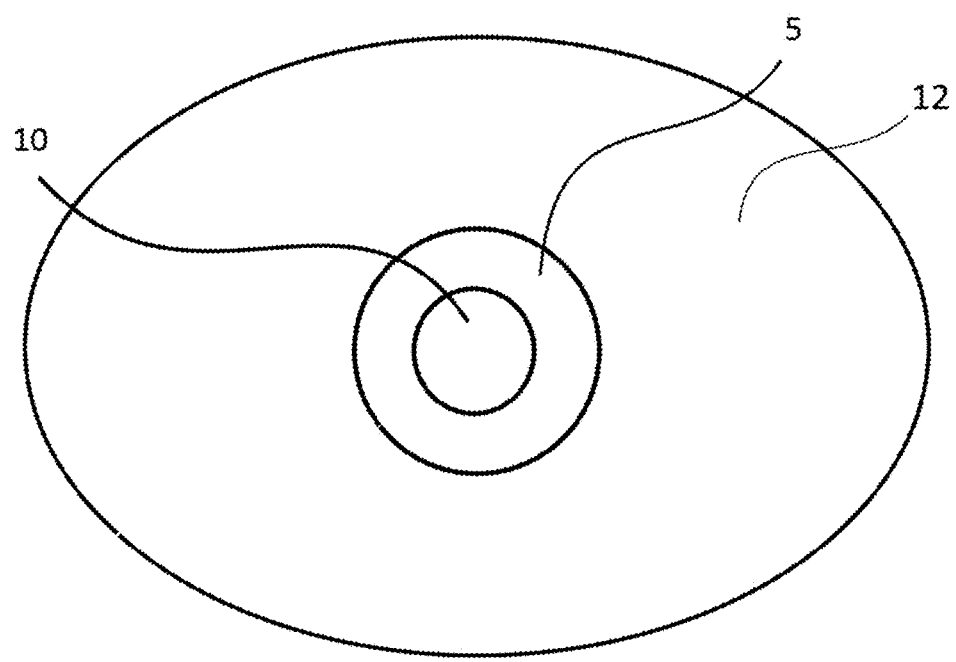
FIG. 2 shows a bottom view of the first embodiment of the electrode.
Figure 3:
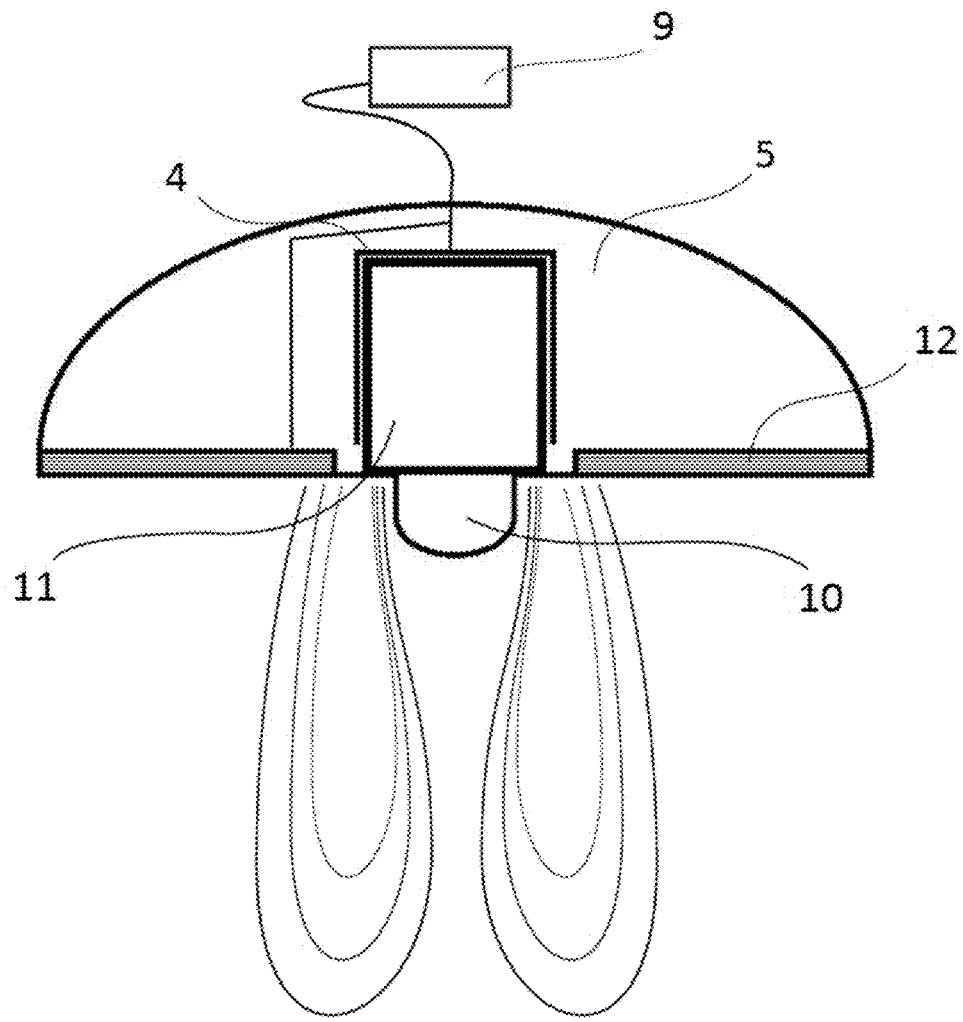
FIG. 3 shows a magnetic field emitted by the first embodiment of the electrode.

Another embodiment of the electrode is represented by an embodiment with a conductive magnet. This example of a geometrical arrangement of active components is shown in FIG. 1 and FIG. 2, wherein it includes a diamagnetic wedge 10, the main magnet 11, and the pole piece 4. These components provide increased penetration depth of the electric current flowing between the diamagnetic wedge 10 and the passive conductive contact 12, even at low stimulation currents. They are, due to their configuration, capable of linearizing and concentrating parabolic electric field lines in an axial direction around the axis of the main magnet 11. This results in an ion channel, limited in the diameter and direction of ion movement by the magnetic field. Thus, as carriers of electric charge into the intercellular spaces, the ions move along trajectories determined by magnetic field lines. The diamagnetic wedge 10 has two functions. It diverts magnetic field lines from the axis of the main magnet 11 and provides electrical connection with the skin. In this example, the diamagnetic wedge 10 is made of copper and is in the shape of a cylinder, which is rounded at the end adjacent to the tissue for better contact with the skin and for maximum possible patient comfort. As is evident from FIG. 2, the diamagnetic wedge 10 is positioned so that it is completely or at least substantially surrounded by the magnetic field of the main magnet 11. In order to perform its function while being easy to maintain, it is further covered with a layer of gold or other non-toxic and inert material conducting electricity well. The outer casing and the base of the main magnet 11 away from the skin are preferably surrounded by the pole piece 4 made of diamagnetic material. The diamagnetic wedge 10 on the side away from the skin is connected to the main magnet 11 by means of a conductive adhesive or other conductive connection, and, in addition to the above effects, it also prevents a so-called magnetic short circuit on the side of the main magnet 11 oriented towards the skin. In this example, the passive conductive contact 12 of the electrode is embodied as a thin copper sheet, which can be gold plated but other diamagnetic materials such as silver, gold, bismuth, carbon and electrically conductive plastics of various compositions can be used as well. In the figures, the passive conductive contact 12 of the electrode is annulus-shaped and is attached to the fixing element 5, thereby being separated from the main magnet 11 by a gap filled with the same insulating material of which the fixing element 5 is made. In other embodiments, however, the passive conductive contact 12 can be represented by various types of conductive fabrics or any conductive gel or other conductive material commonly used in medicine. In this example, the main magnet 11 is represented by a neodymium magnet (NdFeB). The main magnet 11 consists of one or, in alternative embodiments, of several adjacently arranged magnets, and it is oriented with its north pole facing the tissue. The fixing element 5 and the passive conductive contact 12 of the electrode are made of materials intended for medical use, which are preferably waterproof and resistant to frequent sterilization. FIG. 3 shows the field lines of the electrostimulation device.

A source 9 of voltage is connected to the device between the diamagnetic wedge 10 and the passive conductive contact 12. Its output values of the signal shape and frequency are adjustable. Preferably, frequencies between 0.1 to 100 Hz can be used, and the pulse can be monophasic or biphasic. Pulse shape can be rectangular, sinusoidal or triangular with exponential inclines or declines and the pulse widths from 0.1 to 5 ms or precisely from 1 to 3 ms with an amplitude from 0 to 50 mA. A frequency between 1 to 15 Hz or, more precisely, 2-7 Hz appears to be the most preferred and very efficient, but each patient may respond optimally to a different frequency, so individual adjustment plays an important role.

Another example is a solution of electrostimulation device which does not contain a diamagnetic wedge 10, and is thus suitable also for other applications, in addition to those described above, such as for stimulating superficial nerves, improving the absorption of substances through the skin, and for a better supply of nutrients to the skin. For non-invasive electrical connection with the tissue, this embodiment sees the base of the main magnet 11 as being in direct contact with the skin. While in the embodiment illustrated in the figures, on the side facing the skin, i.e. on the side intended to be applied to the skin, the main magnet 11 is adapted for non-invasive electrical connection to the tissue by being equipped with a diamagnetic wedge 10. In this embodiment, the main magnet 11 is, on the side facing the skin, i.e. on the side intended to be applied to the skin, adapted for non-invasive electrical connection to the tissue by being coated at least on a part of the surface with epoxy resin, conductive plastic, or metal such as nickel, silver, carbon, gold or platinum. This is again a bipolar electrode, in which the main magnet 11 and the passive conductive contact 12 are firmly fixed in the fixing element 5 relative to one another, which is advantageous for re-stimulation of a particular site. As with the other embodiments, it is possible to enhance the effects of the magnetic field using pole piece 4 of the main magnet 11 as described above, but its use is not required for all applications.

The fixing element can be made of plastic, rubber, or other material such as a neoprene strap or disposable tape, both of which being glued together or otherwise attached.

The device may be used for a treatment of urgent types of incontinence or an overactive bladder (OAB), for example caused by hypersensitivity in nerve receptors in the bladder. Due to a malfunction in these receptors, even when the bladder is one-quarter full, the receptors in the brain will send a false signal leading to an urgent bladder contraction. The patient then feels an immediate need to go to the toilet or, in some cases, urine will leak. The purpose of stimulation using the proposed device is the transmission of signals through afferent paths to the brain, which will then restart the receptors in the bladder and these will then return to a normal state. Further the device may be also used for a treatment of neurodegenerative diseases such as Parkinson's, Alzheimer's, Huntington's disease, Amyotrophic lateral sclerosis (ALS) or Motor neuron disease.

The electrode 15 system and the detector 14 may be connected via the control unit 13, which controls the entire system. As mentioned above, the system may include a single electrode 15, or more electrodes 15. These can include transcutaneous, percutaneous, or implantable electrodes. Even when using a single electrode 15, it is possible to determine the optimal frequency; however, for clinically effective stimulation of the peripheral nerves, may be necessary to use two electrodes. The electrode 15 may be connected to the pulse generator 18. The latter can be of two types. The generator 18 is either directly a part of the electrode 15, i.e. it is located within the electrode 15, or it is external. An external pulse generator 18 can be located in the controller 16 or, in case of implantable electrodes 15, it remotely powers the stimulator.

Figure 6:
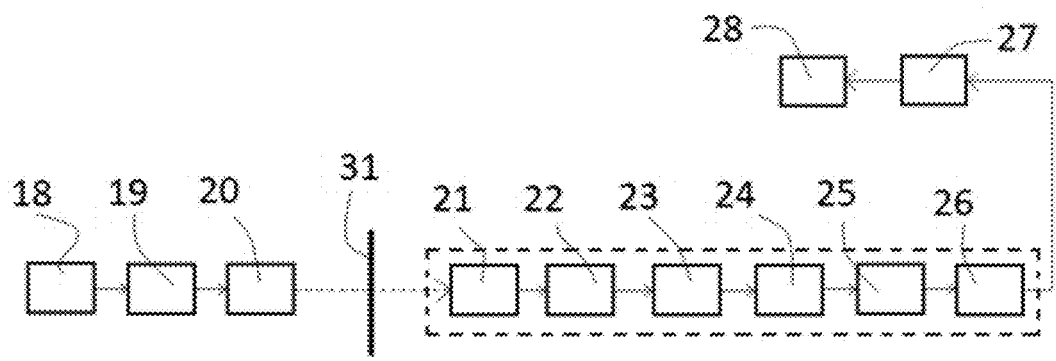
FIG. 6 shows an assembly of the optical sensor in the detector.

The detector 14 consists of a sensor 17. In the embodiment of the present disclosure, the sensor 17 is an optical sensor 17. The optical sensor 17 can have several embodiments, but most preferably it is an optical barrier. An optical sensor 17 assembly is shown in detail in FIG. 6 and is described below in the description of the present disclosure. In general, the optical barrier may include a transmitter and a receiver. The transmitter may include a generator 18, an amplifier 19 and an infrared diode 20 with the optics. The generator 18 may be set to a frequency of 38 kHz. The receiver may include a diaphragm 21, a converging lens 22, an infrared filter 23, a preamplifier 24, a frequency filter 25, a demodulator 26, a level converter 27 and a programmable retarder 28. The frequency filter 25 may be set to 38 kHz. The following parts can be implemented as one component: converging lens 22, infrared filter 23, preamplifier 24, filter 25 and frequency demodulator 26. In this system of transmitter and receiver, the foot 31 may be located between the transmitter output and the receiver input. Other types of optical barriers, such as a reflection optical barrier, are not excluded by the present disclosure. When using a reflection optical barrier, the optical sensor 17 can consist of one sensor 17 or more optical sensors 17 variously spaced on the detector 14. Each optical sensor 17 of the reflection optical barrier is a transmitter and a receiver at the same time. This makes it possible to detect an object, which gets into the vicinity of said sensor 17. The first advantage of an embodiment with multiple optical sensors 17 is that the detector 14 does not need to be set up by the operator as precisely for the patient as when using only one sensor 17. Another advantage is that more detailed information regarding movement is received from several sensors 17, which can be further processed by the control unit 13 in detail. In general, the use of an optical sensor 17 is advantageous in terms of simplicity of use because the sensor 17 detects objects with good accuracy even when the distance from the sensor 17 can vary each time by a few centimeters. These optical sensors 17 are based on the transmission of light in the infrared or other spectrum. The sensors 17 may also be supplemented with a polarizing filter. In addition to a standard infrared sensor 17, a camera can also be used as an optical sensor 17. The camera may include a CCD or CMOS camera with sufficient resolution. Further, the optical sensors 17 can be configured to function without modulation of the signal, with modulation of the signal for increased resistance to overloading the optical barrier by ambient light, or in the infrared region with modulation of signal for increased resistance to overloading the optical barrier by ambient light.

In one possible configuration, the sensors 17 can be arranged one after another. The sensors 17 are placed on the holder, via which they are firmly attached to the rest of the structure. The holder with the sensors 17 can be adjusted by means of a tightening or locking element. Then the whole system records the movements of the lower limbs, which are in its vicinity.

Figure 7:
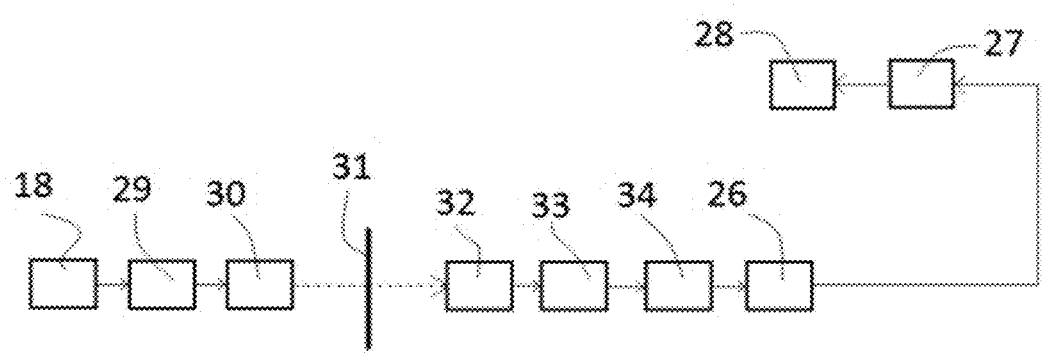
FIG. 7 shows an assembly of the ultrasonic sensor in the detector.

In an alternative embodiment, the sensor 17 is used as an accelerometer, which is attached to the patient's body. The use of an accelerometer is more user-friendly than other sensors. The accelerometer can be attached to the patient's body using a band to which the accelerometer can possibly be incorporated into. Further, the accelerometer is capable of detecting small changes in position. The accelerometer is attached to a part of the leg and the movements resulting from the stimulation are measured by the accelerometer. In an alternative embodiment, capacitive, inductive, thermal, magnetic or ultrasonic sensors 17, direct use of an electromyograph may be used. The disadvantage, compared to optical sensors 17, is the smaller distance at which the sensor 17 can detect an object. An example of an ultrasonic sensor 17 is shown in FIG. 7. Such a sensor 17 includes a generator 18 of 50 kHz, an exciter 29, a primary piezo element 30 and a secondary piezo element 32 at a resonance frequency of 50 kHz, an amplifier 33, a frequency filter 34 of 50 kHz, a demodulator 26, a level converter 27 and a programmable retarder 28. In the case of the sensor 17, the limb 31 is located between the first and the second piezo elements.

The advantage of the sensor 17 providing a digital signal is also that the analog sensors 17 can record the movements induced by the device only via a contact. When recording the induced movements, the contact sensors 17 do not provide a high-quality information, because they naturally interfere with the observed phenomenon. In some cases it results in an echo within the sensor 17 caused by multiple recording of the same movement. Ultimately, this leads to poor detection quality and errant determination of improper frequency stimulation, or a different characteristic of voltage for stimulation. Moreover, mechanical sensors 17 also need additional components to provide a clear, noise-free signal.

The contactless sensors 17 or the accelerometer can be used without any modification between patients. For example, when measuring the induced spasmodic movement of the feet, the measurement must be individually customized to the patient. The feet and physiology of the movements are different for each patient. When using analog sensors 17, such customization is performed mostly by mechanical/manual re-setting of the sensor 17. This requires technical skill on the part of the operator, usually a doctor. As a result, treatment duration and risk of incorrect recording by the sensor 17 are increased.

For proper treatment efficiency, the sensor 17 may be capable of sending the information related to frequency and preferably also other information related to the patient's body motion, such as range of motion or speed. Misuse of the sensors 17, usually contact sensors, as well as directly switching the stimulation of the patient, constitute a significant risk and, due to their error rates, do not result in proper therapy. They do not provide any information about frequency or other parameters, such as range of motion or speed, but they directly affect the activity of the electrode 15. If the system is operating with information on the frequency of movement of a part of the patient's body, it can be software-configured to various configurations and can process the information differently. This, inter alia, may also provide other advantages, which are described further below. In order to send the information on movement frequency, the control unit 13 may be provided with digital information. Such a device as per the present disclosure, can be realized in two ways. Either the direct output from the sensor is 17 is digital, or the analog output is connected to the A/D converter, which converts the analog signal to a digital signal and sends it to the control unit 13.

With a digital signal from the sensors 17, the issue of adapting the measurement for each patient does not arise. All the situations in this case are encompassed in the setup of the control unit 13, which takes individuality into account in advance, and the output from the sensors 17 is processed so that it gives the relevant information without any mechanical re-setting of the detector 14. This applies to both the contactless sensors 17 and the accelerometer, which can be attached to the foot 31.

The sensor 17 for detecting movement of the stimulated limb sends the information to the control unit 13. Here, the information is processed for further use. The control unit 13 may use the information to directly control the electrodes 15 attached to the patient as feedback for effective neuromodulation of peripheral nerves. The induced movements of the legs may provide clinical information that the set frequency of stimulation current is correct. Thus, the control unit 13 may be guided to read the frequency spectrum between the preset limit values. These values may be already factory-set, and they may be 1 Hz and 100 Hz. The control unit 13 may control the electrodes 15 in two phases. These phases may be the recognition phase and the therapeutic phase. In the recognition phase, the device of the present disclosure searches for an ideal frequency or other parameters of the course of current for the individual patient based on the feedback from the sensor 17. The control unit 13 system may include the set rules, defining at what point the frequency of neuromodulation is considered optimum for the patient. Ideally, it is possible to detect each stimulus as a twitch. If the control unit 13 recognizes the ideal frequency, it may be switched to a therapeutic regime. In this mode, the control unit 13 maintains the detected frequency, thus leading to stimulation of the peripheral nerves without further changes. This phase can typically take 30 minutes. In some cases, for sufficient efficiency of the clinical procedure, this may take only about two minutes. The control unit 13 can be set to include such a condition that once the ideal positive feedback linkage from the sensors 17 disappears, the control unit 13 is switched back to the first recognition phase, and it sets the neighboring frequencies to initially identified frequencies.

In addition to frequency, the control unit 13 may set other parameters of the pulse as well. One of them is the pulse length, which is between 0.1 and 10 ms. Another factor controlled by the control unit 13 is pulse shape. The control unit 13 may also set the voltage polarity ranging from positive to negative. Unlike the approach of stimulation by DC, the biphasic current does not cause electrolysis of tissue, and electrolysis presents a problem for sensitive patients, as it potentially leads to skin problems (irritation of skin, infection). The control unit 13 may be set in such a way that it calculates the optimum flow of the pulse current x with opposite polarity in order to cancel the effect of electrolysis. This mechanism is also known under the term "charge-balanced pulse". This feature makes the device safer.

In one aspect, the control unit 13 may set the flow of pulse rounds or pulse bursts. This is, for example, 20 pulses applied over a very short time. In terms of a longer time interval, these pulse bursts appear as a single pulse of an irregular shape.

For the above-described pulse setting, a control unit 13 may command these parameters is required. As an input for the specific setting, the control unit 13 may use the information from the controller 16 and the information on frequency of limb movement from the sensor 17.

Clinical studies have revealed that, for effective treatment, it may be necessary to repeat the therapy in a patient suffering from incontinence roughly five times before permanent improvement can be achieved. This requires the patient to be subjected to therapy with time breaks while inevitably passing through both the recognition and the therapeutic phases again; therefore, the control unit 13 includes a memory unit where the staff can store data for a single patient, including information relating to at least one identified ideal parameter for a given patient. The memory of the present disclosure can be any kind of data storage, either a local or remote one. These storage devices include HDD and SSD hard drives, flash memories, memory cards, RAM devices, CDs, DVDs, Blu-ray™ discs, etc. The remote storage units include the ones that are accessible only by connecting the device to a local network or the internet, GSM, such as cloud storage. Local network, internet or GSM can all be understood as a network service. The network may by created also by a number of presented neuromodulation devices, wherein the first of the neuromodulation devices is connected to remote storage, and the others are connected to this neuromodulation device. The indirect connection of other neuromodulation devices connected to the remote storage is preferably wireless. The other neuromodulation devices communicate with the remote storage unit through the first neuromodulation device. The first neuromodulation device then redirects the data from the remote storage unit to the other neuromodulation devices connected to the first neuromodulation device as per the identification part of the communicated data.

The stored information about the patient may effectively reduce the time required for performing the procedure, and it can also serve as additional home therapy. In some cases, the patient may buy the electrodes 15 intended for domestic use for themselves, allowing the patient or a family member to apply them. This type of device also may have a control unit 13 which can use the stored information on the identified stimulation parameter and adjust the therapy accordingly. The entry of this information to the device depends on the selected storage method, which is not particularly limited by the present disclosure. In a preferred embodiment, it can be, for example, an SD memory card which is inserted into the device in the doctors office to identify the ideal stimulation parameter and also into the device for home use, where the proper therapeutic settings are as per the identified stimulation parameter. In another preferred embodiment, the selected storage device can be e.g. cloud memory. The stimulation parameter can be entered through the device to the cloud storage and made accessible at the doctor's office or in home therapy by the same or any other device. The cloud storage and the stimulation parameter entered thereto may also be accessible through a computer, tablet, mobile phone or other electronic device connected to cloud storage.

In addition to reducing the duration of therapy, storing patient data has other advantages. Thanks to the determination of individual stimulation parameters, there is no need to store this information in another patient file. On the patient's next visit, it is only necessary to recall the information automatically from the system with no search being necessary. This also prevents a possible error arising from poor handwriting. An incorrectly set parameter does not lead to improvement of the patient's condition. The system comprising such information can be further enhanced by including the statistics that are directly related to the use of the device. In addition to information on a particular frequency, the system stores other parameters affecting the pulses described above, such as the polarity of pulses, their length, shape, and others. These statistics are also saved to memory where the therapeutic information is available for a particular patient. Then, the amount invoiced to the patient is always determined correctly and fairly. The same applies to the amount invoiced to the office by the suppliers in cases when the device in the office is charged according to the number of treatments performed. It is also possible to work with such information as a high-quality source for producing such statistics, which can then be used both for clinical purposes, making it possible to predict the improvement in the patient's condition in the future on the basis of the recorded treatment. Furthermore, these statistics are useful for determining the usability of the device, calculating the avoided costs associated with alternative treatments, calculating service intervals, and so on.

The control unit 13 of the present disclosure can be unitary, or the device can include several control units 13, e.g., one for the detector 14 and another for controlling the electrodes 15. If the device involves several control units 13, these units may be equipped with communication protocols for continuous information exchange. As a part of the therapeutic device, the control unit 13 may also serve as a decision-making actor instead of the doctor. In analogue systems, it was necessary that the doctor directly set the parameters depending on the observation of induced movements or depending on the sensor 17 output for same. This leads to lower therapeutic efficiency.

The advantage of sending the movement frequency information from the sensor 17 to the control electronics is an increase of the safety and efficiency of the product. With mechanical sensors 17 connected to the electronics, which use only the amplified signal from the sensor 17 as an excitation signal for stimulation, a potentially dangerous situation can arise. Due to higher requirements for medical devices, such an approach may not be feasible in clinical conditions; therefore, a device may comprise a control unit 13 with included commands for various situations, thus ensuring an increased security. These commands can be a part of the software or firmware of the control unit 13 depending on its technical level. The mechanical sensors 17 are also prone to error conditions. They represent a high risk, specifically in cases in which the recording is used as input for stimulation by the electric current. These error conditions can lead to muscle spasm or, worse, to local burns to the patient at the site of the electrode 15. The electronics able to ensure greater security may require the connection of sensors 17 providing digital information. Using a mechanical sensor 17 and safe electronics would require another link between the sensor 17 and the control unit 13, which would increase the total price of the device as well as a possible increased failure rate and inaccuracy by adding another element to the system.

The device may also involve a controller 16. In general, the controller 16 may represent an user input for controlling the control unit 13, and this input can take various shapes and forms. The controller 16 may comprise the control unit 13 described above. In alternative aspects, the control unit 13 may be located outside the controller 16. The controller 16 may be part of the structure of the entire device but does not need to be fixed firmly. The controller 16 can be loosely attached to the structure, but it can be lockable with respect to the support structure in at least one position. In one aspect, the controller 16 may involve a display device and a button. The button connected to the controller 16 can be a multistep one, enabling more than one instruction to be given depending on the movement of the controller 16 chosen by the operator. The display device may be used for transferring the information to the operator. After beginning therapy, the display device can show the instructions for using the device, so that the therapy is as effective as possible. These can be in the form of a sequence of instructions that are shown on the display device one by one by the operator's clicking on the button of the controller 16. The displayed information may be controlled by the control unit 13 of the device.

The method of treatment of incontinence or neurodegenerative diseases such as Parkinson's, Alzheimer's, Huntington's disease, Amyotrophic lateral sclerosis (ALS) or Motor neuron disease using the neuromodulation device described above and also other similar neuromodulation devices is further disclosed. Symptoms of an overactive bladder or at least one of the above defined neurodegenerative diseases are, according to the present disclosure, treated using a neuromodulation device comprising at least two active electrodes capable of generating electrical pulses. The first step of the present disclosure is attaching first one active electrode to a patient's leg and attaching a second active electrode to any of the patient's legs. Attaching of any of the active electrodes is to be understood as attaching a removable electrode to the patient's skin (transcutaneous) or attaching any of the active electrodes to the patient's body by penetrating the patient's skin percutaneously or attaching any of the active electrodes by implanting the active electrodes into the patient's leg for long-term implantation. Further, the first electrical pulses are generated in the first active electrode into the patient's body and the second electrical pulses are generated in the second active electrode into the patient's body. Further, the present disclosure may involve a step of setting a flow of the current of the pulses. The present disclosure may further include a step of synchronizing the timing of each pulse.

After generating the electrical pulses, the pulses may be delivered to the branches of the patient's nerves, thus stimulating the nerves and delivering the stimulus in the form of the pulse to the target area. The target area may be the sacral plexus or the sciatic nerve. In one aspect, the first electrical and second electrical pulses are generated in turns, thus the interval of the electrical pulses can be as follows: the first electrical pulse, then the second electrical pulse, then the first electrical pulse, and so on. Alternatively, the interval can be as follows: the second electrical pulse, the first electrical pulse, the second electrical pulse and so on. In some of the preferred embodiments, the electrical pulses can be generated simultaneously at the same time or can be generated independently, such as the first electrical pulse, the second electrical pulse, the first electrical pulse, and so on. In one aspect one of the first electrical pulses and one of the second electrical pulses reach the target area simultaneously. The simultaneous effect of two independently generated electrical pulses may bring higher effectivity of the treatment compared to the prior art. According to the present disclosure, more than two active electrodes may be used, wherein a third active electrode may be attached to the patient's body, for example, a third active electrode capable of generating electrical pulses may be attached to either of the patient's legs. The third electrode may generate the third electrical pulses, which may be synchronized so that one of the third electrical pulses, one of the second electrical pulses and one of the first electrical pulses reach the target area simultaneously. Similarly, more active electrodes can be attached to the patient's body in order to generate electrical pulses.

The active electrode may be an electrode such as the electrode described previously and illustrated in FIG. 4, comprising a magnet 3, a pole piece 4, the first pole 1 of the electrode and the second pole 8 of the electrode. Another embodiment of the electrode is the electrode shown in FIG. 1. and described previously. Preferably, the electrodes used are transcutaneous as in the two electrodes described previously or another embodiments of transcutaneous electrodes. Transcutaneous electrodes are advantageous mostly because their usage does not require invasive procedures. In yet another embodiment of the disclosure, the percutaneous electrodes capable of penetrating the patient's skin and capable of generating electrical pulses are used as active electrodes. In yet another example of the embodiment of the present disclosure, the electrodes may be long-term implantation electrodes. The electrodes, for example, the first electrode, the second electrode and the other electrodes can involve one or more conductors. The active electrodes of any type are characterized in that they may be capable of generating electrical pulses or capable of delivering the electrical pulses generated by a pulse generator to the body of the patient. The generator may be either directly a part of the electrode, i.e. it is located within the electrode, or it is external. An external pulse generator can be located in the controller or, in case of implantable electrodes, it remotely powers the stimulator. In the embodiment of the present disclosure using electrodes for long-term implantation, the electrodes can be inductively "charged". In this embodiment, the external pulse generator is connected to an inductor, and the electrical pulses are generated in the electrodes by the magnetic field created by the inductor.

In an aspect of the present disclosure, the active electrodes are attached in proximity to the branches of a peripheral nerve so that the electrical pulses generated by any of the electrodes are capable of delivering electrical pulses to the nerve. When using transcutaneous electrodes, the electrodes are placed, for example, in the area of the knee so that the surface of the electrodes is facing a branch of peripheral nerve through the tissue. When using the percutaneous electrodes or the electrodes for long term implantation, the electrodes may be placed within the vicinity of the branches of a peripheral nerve while not directly touching the branches of a peripheral nerve.

In the method of the present disclosure, any of the following nerves are stimulated: the lumbosacral plexus, sciatic nerve, common peroneal, tibial nerve, pudendal nerve, superior gluteal nerve, inferior gluteal nerve, posterior cutaneous femoral nerve, obturator internus nerve, piriformis, quadratus femoris nerve, plantar nerve or coccygeal nerve. Most advantageous in treatment of the symptoms of an overactive bladder or a neurodegenerative neurological disease such as Parkinson's, Alzheimer's, Huntington's disease, Amyotrophic lateral sclerosis (ALS), Motor neuron disease is stimulation of the peroneal nerve, pudendal nerve, tibial nerve or any combination of the aforementioned nerves. Stimulation of the nerves is achieved by sending the electrical pulses through the branches of peripheral nerves and distributing the nerve stimulus to the target area of, for example, other sacral plexus or the sciatic nerve. The electrodes can be, as per the present disclosure, attached to the patient so that the first active electrode is attached to the first branch of a sciatic nerve and the second active electrode is attached to a second branch of the sciatic nerve; in other embodiments, multiple active electrodes can be attached to multiple branches of the sciatic or other nerves in order to stimulate the target area. The active electrodes can be both attached to the same leg or be each attached to a different leg of the patient. In some cases, attaching the active electrodes to different legs of the patient increases the healing effect, as the simultaneous effect of stimulation is more easily achievable.

In the method of treatment, there may be further a grounding conductor placed on the patient's body. Preferably the grounding conductor is in the form of a pad. The grounding pad can be placed anywhere on the patient's body. As per the present disclosure, the grounding conductor may be placed on the patient's suprapubic, hypogastric or sacral area. By placing the grounding conductor in said areas, the healing effect of the method increases. For the grounding conductor attracts the first and second electrical pulses, thus the target area may be reached more effectively. Additionally, the grounding conductor can be configured for generating the electrical pulses, wherein in some embodiments, the grounding conductor generates positive electrical pulses and thus has a calming effect on the patient's bladder.

In the presented method, a variety of electrical pulses may be used. In one aspect of the present disclosure, the following limitations may be used for the electrical pulses. The frequency of the first electrical pulses, second electrical pulses or, in some embodiments, the pulses generated by a third, a fourth or other electrodes is between 0.1 Hz and 100 Hz. Pulse width of said pulses is between 0.1 ms and 5 ms, and the current of said pulses is between 0 mA and 250 mA, with the voltage of said pulses being between 0 V and 90 V. As every patient reacts to treatment differently because of different physiology, the parameters of pulses therefore vary for individual patients. In one of the preferred embodiments, the parameters vary over the course of the treatment of the patient according to the patient's response to the treatment. Adjustment of the parameters can be made by the person providing the treatment or automatically by means of a control unit having a suitable algorithm. For most patients, the best treatment results may be achieved by using the following parameters of said pulses: a voltage frequency of between 2.5 Hz and 60 Hz and a pulse width between 0.1 ms and 2.5 ms. The Current of said electrical pulses also depends on the type of the electrode used and its surface. Using electrodes which have an active surface of more than 2 $cm^2$ achieves the most effective treatment results using a current of the said electrical pulses between 15 mA and 250 mA. Using electrodes which have an active surface of between 0.5 $cm^2$ and 2 $cm^2$ achieves the most effective treatment results using a current of said pulses between 0 mA and 15 mA. Using electrodes which have active a surface of less than 0.5 $cm^2$ achieves the most effective treatment results using current of said pulses between 0 mA and 5 mA. The shape of said electrical pulses may be also important for improving treatment results; most effective is, as per the present disclosure, a shape of the electrical pulses having a steep incline. Therefore, an advantageous shapes of said electrical pulses may be substantially rectangular or substantially of the shape of right triangle. Said pulses may be monophasic or biphasic.

In one aspect of the present disclosure, the flow of current may be set correspondingly to a biofeedback signal. Such a biofeedback signal can be visual or determined means of a sensor. Typically, the biofeedback can be the form of twitching in the patient's lower limb.

In order to ensure highly effective treatment, said pulses may be applied to the patient's body in a synchronized manner so that nerve stimuli generated in the patient's nervous system by the first electrical pulses and the nerve stimuli generated in the patient's body by the second electrical pulses reach the target area simultaneously so that the nerve stimulus generated in the patient's nervous system by any of the first electrical pulses and the nerve stimulus generated in the patient's nervous system by any of the second electrical pulses reach the target area at the same time. In other advantageous aspect of the present disclosure, nerve stimuluses may be also generated in the patient's nervous system by tertiary electrical pulses and/or by any further electrical pulses generated by any other active electrodes, which are synchronized. Synchronization of the pulses may provide more effective treatment, so that quicker recovery and shorter treatment sessions are preferably achieved. Synchronization of the pulses can be, according to one aspect, achieved by means of an algorithm stored in the memory of the control unit, wherein the algorithm sets the timing of the generation of the electrical pulses. Multiple inputs can be acquired by the algorithm, such as data from a sensor monitoring biofeedback, duration, and parameters of the first electrical pulses, second electrical pulses and any other electrical pulses, data of the previous treatment sessions of the patient and other relevant data.

A method of positioning the electrodes is further disclosed, wherein, firstly, an active electrode is attached to the patient's body. Preferably but not exclusively, the attachment is made in the knee area of the patient. After the attachment, electrical pulses may be generated in the active electrode. After and/or during the generation of these electrical pulses, the reflex movement of the patient's body part is monitored. The reflex movements of the patient's body part are, for example, twitches of the lower limb, and such monitoring can be done either visually or by sensor. The monitored reflex movement, such as the twitching of the patient's lower limb, may be thereafter, or during the monitoring, compared to the expected reflex movement. Determination can be made by the person or by an algorithm. For example, the algorithm compares the data acquired by the sensor and compares it to the data stored in the memory of the control unit. For example, such data can be represented by the number of twitches of the limb per period of time. In case the number of twitches of the lower limb is the same or higher than the number of twitches of the lower limb stored in the memory of the control unit, the reflex movement of the patient's body is considered to be sufficient. Subsequently, the control unit can visually, acoustically or tactually inform the person of the achievement of sufficient or insufficient reflex movement of the patient's body part. If the reflex movement of at least part of the patient's body is insufficient, the electrode may be relocated on the patient's body and the steps are repeated. This method enables the user to precisely position the active electrode in order to stimulate the nerves of the patient more effectively.

The method described above is also suitable for treatment of other medical conditions, such as and not limited to, painful bladder syndrome, fecal incontinence, Low Urinary Tract Dysfunction and neurodegenerative diseases such as Parkinson's, Alzheimer's, Huntington's disease, Amyotrophic lateral sclerosis (ALS) or Motor neuron disease.

One of the possible illustrative embodiments of the present method is further disclosed. For purpose of this illustrative embodiment, the active electrode is of a transcutaneous type and the neuromodulation device involves two active electrodes, a grounding electrode, a memory unit, a control unit, a sensor for monitoring the reflex movement of at least a part of the patient's body, such as an accelerometer communicatively coupled to the control unit, and a controller for controlling the neuromodulation device. A person, such as the patient or the patient's physician, attaches the active electrode onto the patient's body. The person may attache the first electrode, for example, in the knee area of the first leg in such manner that the first electrode's active surface faces approximately the peripheral nerve. The person may further places the grounding electrode, preferably in the form of a pad, on patient's suprapubic, hypogastric or sacral area. The person may further place the accelerometer on the patient's leg. The then person may activate the device to start generating the first electrical pulses. In this illustrative embodiment, the neuromodulation device informs the patient of the sufficiency of the induced movements of the part of the patient's body, in this embodiment, the leg. The initial pulses may be generated with parameters according to the previous treatment sessions of the patient; in cases in which the parameters are not stored in memory, the control unit sets the parameters based on pre-set default parameters. The parameters of the first electrical pulses may be any of the following frequency intervals: between 0.1 Hz and 100 Hz, a pulse width of between 0.1 ms and 5 ms, a current of between 0 mA and 250 mA, with a voltage between 0 V and 90 V. The control unit may generate the first electrical pulses and changes the parameters of the pulses. In case, after a predefined number of first electrical pulses and number of variations of parameter values, the movement of the leg being monitored by the accelerometer is insufficient, the device may inform the person, for example, audibly or visually in another manner. For example, by means of a red light, a text display or by means of a predefined sound. The person may then reposition the first active electrode and repeats the process until the movement of the leg is sufficient. The neuromodulation device may inform the person of sufficient reflex movement either audibly or visually, for example, by means of, say, a green light or by a text display. Once the first active electrode may be precisely attached, the person attaches the second active electrode to the patient's body. In this illustrative embodiment, the second active electrode may be attached to the patient's second leg in the knee area in the same way as the first electrode. The second electrode may be further precisely positioned using substantially the same steps as in the foregoing precise positioning of the first active electrode. As both of the active electrodes may be precisely positioned to the patient's body, the first electrical pulses and the second electrical pulses are directed to the patient's body, stimulating the target area. The flow of the pulse current may be set manually or by means of the control unit. Preferably, in this illustrative aspect, the parameters of the first electrical pulses and the second electrical pulses are set via the control unit. In this aspect, the synchronization of the pulses may be achieved by means of the control unit, for example, on the basis of biofeedback, such as the reflex movement of the patient's leg. The parameters of the pulses might vary during the treatment session, depending upon the patient's biofeedback. The treatment session takes typically 15 to 45 minutes.

In this illustrative aspect information regarding the treatment session can be collected and stored in an adjacent or remote memory storage device for further use.

A method of collecting information about usage of a medical device, such as the neuromodulation device described above, other similar neuromodulation devices or other medical devices are further disclosed. The medical device may comprise a memory and a control unit. Such said medical devices can be, for example, therapeutic medical devices, surgical devices or diagnostic medical devices. The method may involve the first step, where information from the control unit is collected, after that the collected information is sent from the control unit to memory. After sending the information to the memory. the information may be stored in a database. The information stored in the database may be later called out from the database, for example, by using a control panel, computer or other electronic device with access to the database. The control unit can communicate with the memory using a variety of communication protocols, such as but not limited to GSM, Bluetooth, radio frequency, infrared communication, LAN, USB and a wireless internet connection. In one aspect, the memory can be remote from the medical device, such being stored on the cloud, remote server or remote data storage. In one aspect, an identification number may be assigned to the medical device and/or to a patient. In one aspect, the identification number is assigned also to the particular information. According to the identification number, the memory can assign payment and suitable treatment parameters for the patient. For example, using a medical device and a memory of a remote type, any medical device can call information about the patient and adjust treatment parameters according to the patient's needs; payment can also be directed accordingly to the patient's identification number. Accessing the remote memory of the medical device can be achieved by connecting to remote memory, such as the cloud, or by connecting to the memory adjacent to the medical device through a connection established in between the medical devices. In one aspect, several medical devices can create a communication network, with one of the medical devices being able to connect to the memory and other medical devices being able to access the memory by communicating with the said one medical device.

In one aspect, the information stored in the database may be sent to the patient's physician and/or to the patient's electronic medical chart. Sending the information automatically or upon the patient's request through the device is convenient for the patient and patient's physician, especially during home treatment applied by the patient himself. The data stored in the database can also be used for evaluating the progress of each user. Also, the information stored in the database can provide a long-term statistical record of the usage of the medical devices. Such feedback may be important for the manufacturer to fine-tune the device accordingly and to have sufficient data for development of the devices. Information used for such long-term statistics, for example, data on usage of neuromodulation devices, may be any the following: the data on the number of users, data on the intensity of usage, on the number of payments, on current intensity or on frequency of pulses.

The inventors surprisingly found the above defined methods may be applicable also for a neuromodulation treatment of neurodegenerative diseases as follows.

The above-mentioned methods may include a method for a neuromodulation treatment of a patient and may be used for the treatment of a neurodegenerative disease. In such case the method for a neuromodulation treatment of a neurodegenerative disease may comprise: attaching a first active electrode to a first patient's leg in the back of the knee area in an expected location of a peroneal nerve of the first leg; attaching a grounding electrode to the patient's body; generating electrical pulses by a pulse generator connected to the first active electrode and the grounding electrode; stimulating by the first active electrode the peroneal nerve of the first leg; and controlling via a control unit a flow of the generated pulses to the first active electrode.

The method for a treatment of a neurodegenerative disease may further comprise: attaching a second active electrode to a second patient's leg in the back of the knee area in an expected location of a peroneal nerve of the second leg; generating electrical pulses by the pulse generator connected to the second active electrode; stimulating by the second active electrode the peroneal nerve of the second leg; and controlling via a control unit a flow of the generated pulses to each of the first and second active electrode.

Alternatively, the method for a neuromodulation treatment of a neurodegenerative disease may comprise: attaching a first active electrode to a first patient's leg in the back of the knee area in an expected location of a tibial nerve of the first leg; attaching a grounding electrode to the patient's body; generating electrical pulses by a pulse generator connected to the first active electrode and a grounding electrode; stimulating by the first active electrode the tibial nerve of the first leg; and controlling via a control unit a flow of the generated pulses to the first active electrode.

Such alternative method for a treatment of a neurodegenerative disease may further comprise: attaching a second active electrode to a second patient's leg in the back of the knee area in an expected location of a tibial nerve of the second leg; generating electrical pulses by the pulse generator connected to the second active electrode; stimulating by the second active electrode the tibial nerve of the second leg; and controlling via a control unit a flow of the generated pulses to each of the first and second active electrode.

In the method for a treatment of a neurodegenerative disease, the neurodegenerative disease may include Parkinson's, Alzheimer's, Huntington's, Amyotrophic lateral sclerosis (ALS) or Motor neuron disease.

Stimulating of the first and the second peroneal nerve may involve a simultaneous stimulation of the first and the second peroneal nerve. Alternatively stimulating of the first and the second tibial nerve may involve a simultaneous stimulation of the first and the second tibial nerve.

Controlling may involve setting voltage and/or current of the generated pulses to invoke a reflex movement of each of the first and the second patient's leg. The grounding electrode may be attached to patients suprapubic or sacral area. The generated electrical pulses may be electrical pulses with a frequency comprised between 2.5 Hz and 60 Hz and the electrical pulses may have a pulse width comprised between 0.1 ms and 2.5 ms. The frequency of the electrical pulses may be comprised between 0.5 Hz and 10 Hz. Thus, the frequency of the electrical pulses may be 0.5 Hz, 1 Hz, 2 Hz, 3 Hz, 4 Hz, 5 Hz, 6 Hz, 7 Hz, 8 Hz, 9 Hz or 10 Hz. The frequency of the electrical pulses may be comprised between 2.5 Hz and 10 Hz. The frequency of the electrical pulses may be comprised between 2.5 Hz and 6 Hz. The voltage of the generated electrical pulses may be less than 90 V and current of the electrical pulses may be lower than 250 mA. Each of the active electrodes may have an active conductive surface attached to a patient's leg comprised between 0.0775 square inch (0.5 $cm^2$) and 0.3100 square inch (2 $cm^2$). Each of the active electrodes may have an active conductive surface attached to a patient's leg less than 0.0775 square inch (0.5 $cm^2$). Each of the active electrodes may have an active conductive surface attached to a patient's comprised between 0.0155 square inch (0.1 $cm^2$) and 0.0775 square inch (0.5 $cm^2$).

The method for a neuromodulation treatment of a low urinary tract dysfunction may further comprise detecting a reflex movement of each of the first and the second patient's leg. The reflexive movement may be a response to the first and/or the second peroneal nerve stimulation. The reflexive movement may be a periodical reflexive movement in a transversal plane of a foot belonging to the respective first and second patient's leg. Alternatively, the reflexive movement may be a response to the first and/or the second tibial nerve stimulation. The reflexive movement may be a periodical reflexive movement in a transversal plane of a foot belonging to the respective first and second patient's leg.

The method for a treatment of a neurodegenerative disease may further comprise monitoring the reflexive movement of each of the first and the second patient's leg; comparing the monitored reflex movement with a pre-set value of an expected reflex movement and based on the comparison determining whether the reflex movement is sufficient.

The method for a treatment of a neurodegenerative disease may further comprise determining frequency of the periodical reflexive movement for each of the first and the second patient's leg. Controlling may then involve an automatic setting of the flow of the generated pulses to each of the first and the second active electrode depending on the determined frequency of the periodical reflexive movement of each of the first and the second patient's leg. The automatic setting of the flow may then involve setting timing of generated pulses to each of the first and the second active electrode so that the periodical movements of the reflexive movement of the first and the second leg are synchronized.

The method for a treatment of a neurodegenerative disease may further comprise collecting information from the control unit about the flow of the pulses and storing the information in a database. The information may comprise current of the pulses, frequency of the pulses and an information of the treatment duration.

The expected location of a target nerve may be a generically known location onto a patient skin closest to the target nerve or inside of the patient body closest to the target nerve. Generic locations of nerves within a human body are known, however, as they differ per person, the expected location of the target nerve might not be the actual closest location to the person's target nerve.

Attaching an electrode to a patient may mean attaching the electrode onto the skin of the patient and/or attaching the electrode into the patient's body.

Exemplary Study Showing an Effect of the Method on Brain

An exemplary study was designed and performed to test that the above-described method and its variances induces desired changes in the neuronal activity in the brain. A total of 22 healthy volunteers were enrolled into the study. All volunteers underwent an active peroneal nerve stimulation using the above-described method, which in all volunteers elicited a motor response in the form of rhythmic movement of both feet in the transverse plane. Subsequently, an identical feet movement was induced in all volunteers passively using a specially designed "sham" device without a simultaneous neuromodulation. This made possible to distinguish changes in neuronal activity during passive feet movements by the "sham" device from changes elicited by the neurostimulation using the above-described method. Simultaneous functional magnetic resonance imaging (fMRI) was employed to measure changes in neuronal activity. The fMRI enables a detection of a local change/increase in blood supply in the brain tissue, which correlates with an increase of a neuronal activity.

The neuromodulation was performed within a non-limiting frequency range of the electrical pulses between 0.1 to 10 Hz, however, similar responses were observed in both higher and lower frequencies. Therefore, the neuromodulation may be performed at 0.5 Hz, 1 Hz, 2 Hz, 3 Hz, 4 Hz, 5 Hz, 6 Hz, 7 Hz, 8 Hz, 9 Hz or 10 Hz.

Two active electrodes were attached one per each leg of the study subjects. Each electrode was attached in the back of the knee of the respective leg. One electrode on one leg may however suffice.

All fMRI data were acquired with a 3T MRI scanner and analyzed using individual and group statistical analysis (p<0.05). Statistical analysis on the individual level assessed twelve selected brain regions and the mask for each specific region was used to acquire statistically significant voxels of activation within these regions. The resulting individual statistical maps were subsequently included in group statistics using a one-sample t-test and an uncorrected threshold of p=0.001.

Results of the study provide evidence that the above-described neuromodulation method elicits a statistically significant activation of specific brain regions such as basal ganglia, limbic system and other that are linked with an early stage of neurodegenerative diseases such as Alzheimer's dementia or Parkinson's disease. The results are summarized in the Table 1 below. The inventors believe that activation of the specific brain regions, associated with an increase in blood flow, helps to improve its metabolism and function. This could lead to the preservation of the neural function (neurorehabilitation) and prevent or delay the onset of clinical symptoms of neurodegenerative diseases.

TABLE 1

| | | | Peroneal | Placebo |
|---|---|---|---|---|
| Brain Stem | | | 0.435 | 0.667 |
| Cerebellum | | R | 0.014 | |
| | | L | 0.004 | |
| Thalamus | | R | 0.599 | |
| | | L | | 0.212 |
| Putamen | | R | 0.033 | |
| | | L | 0.026 | |
| Cingulate gyrus | middle | R | 0.287 | |
| | | L | 0.373 | |
| Insula | anterior | R | 0.022 | |
| | | L | 0.049 | 0.556 |
| | posterior | R | 0.305 | 0.556 |
| | | L | 0.204 | 0.394 |
| Operculum | parietal | R | 0.011 | 0.002 |
| | | L | 0.007 | 0.001 |
| | central | R | 0.048 | |
| | | L | 0.040 | 0.475 |
| Precentral gyrus | | R | 0.021 | 0.005 |
| | | L | 0.012 | 0.002 |
| Postcentral gyrus | | R | 0.029 | 0.023 |
| | | L | 0.027 | 0.015 |
| Supplementary motor cortex | | R | 0.031 | |
| | | L | 0.033 | |
| Temporal gyrus | superior | R | 0.460 | |
| | | L | 0.309 | |
| | transverse | R | 0.392 | |
| | | L | 0.120 | 0.186 |
| Angular gyrus | | R | 0.676 | |
| | | L | | |
| Supramarginal gyrus | | R | 0.001 | 0.124 |
| | | L | 0.001 | |
| Frontal gyrus | superior | R | 0.204 | 0.067 |
| | | L | 0.169 | |
| | middle | R | 0.236 | |
| | | L | | |
| | inferior | R | 0.007 | |
| | | L | 0.046 | |

Figure 8:
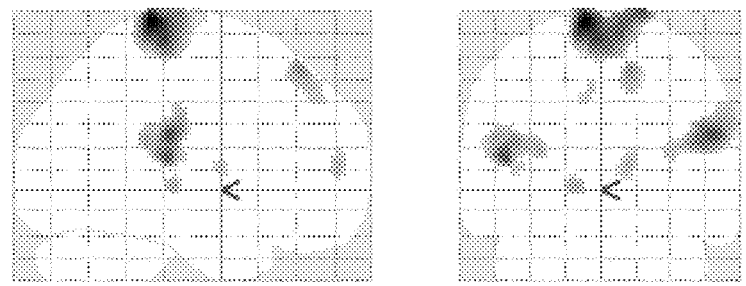
FIG. 8 depicts an exemplary statistically adjusted functional magnetic resonance images (fMRIs) performed on subjects without the actual neuromodulation.
Figure 8:
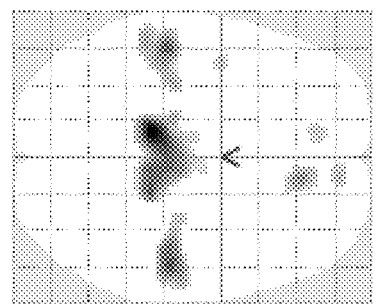
Figure 9:
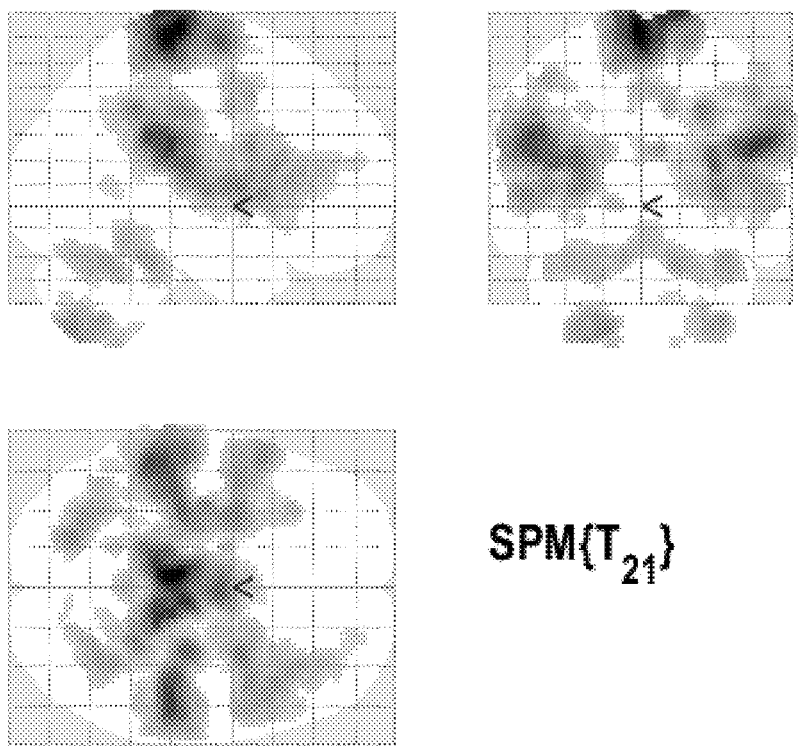
FIG. 9 depicts an exemplary statistically adjusted results of fMRIs performed on subjects during the neuromodulation.
Figure 10:
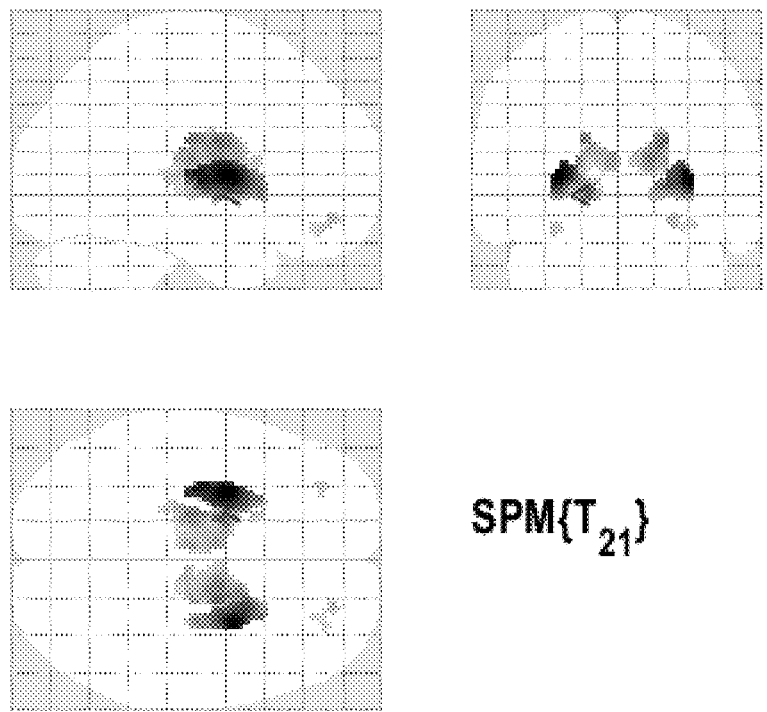
FIG. 10 depicts an exemplary statistically adjusted results of fMRIs focused on detailed analysis of basal ganglia during the neuromodulation.

The results of the study are also graphically presented in FIGS. 8 to 10 depicting statistically averaged details of the fMRIs performed.

More specifically, FIG. 8 depicts statistically adjusted results of fMRIs performed on subjects with a "sham" where a motoric response observed during the peroneal neuromodulation were imitated without the actual neuromodulation. An increase of a blood flow/neuronal activity is visible mostly in superficially located centers including precentral gyrus, postcentral gyrus and operculum as a response to the passive feet movement.

FIGS. 9. and 10. then depict statistically adjusted results of fMRIs performed on subjects during the neuromodulation.

More specifically FIG. 9. shows an expected increase of the blood flow/neuronal activity in the cortical centers involved in the control of the lower limbs (both motor and sensory). In contrary to the "sham stimulation", there is an evident significant increase of the blood flow/neuronal activity in deep brain centers associated with the lower urinary tract function including cerebellum, putamen, insula, supplementary motor cortex and frontal cortex. FIG. 10. shows the results after applying the specific software mask, that allows for detailed analysis of the basal ganglia. There is a significant increase of blood flow/neuronal activity detected during peroneal neuromodulation.

Therefore, Table 1. as well as both FIG. 9. and FIG. 10. confirm that peroneal neuromodulation leads to a significant increase of blood flow/neuronal activity in the deep brain structures including midbrain and basal ganglia playing crucial role in the pathogenesis of the several neurodegenerative diseases such as Alzheimer's dementia or Parkinson's disease.

LIST OF REFERENCE SIGNS

1—first pole of the electrode
2—wire
3—magnet
4—pole piece
5—fixing element
6—nut
7—adapter
8—second pole of the electrode
9—source
10—diamagnetic wedge
11—main magnet
12—passive conductive contact
13—control unit
14—detector
15—electrode
16—controller
17—sensor
18—generator
19—amplifier
20—IR diode
21—diaphragm
22—converging lens
23—IR filter
24—preamplifier
25—frequency filter
26—demodulator
27—level converter
28—programmable retarder
29—exciter
30—first piezo element
31—foot
32—second piezo element
33—amplifier
34—frequency filter

The invention claimed is:

1. A method for a neuromodulation treatment of a patient having an either one of Parkinson's, Alzheimer's, Huntington's disease, Amyotrophic lateral sclerosis and Motor neuron disease, the method comprising:
attaching a first active electrode to a first leg of the patient in the back of the knee area in an expected location of a peroneal nerve of the first leg;
attaching a grounding electrode on the patient's body;
generating electrical pulses by a pulse generator connected to the first active electrode and a grounding electrode;
stimulating by the first active electrode the peroneal nerve of the first leg and activating via the stimulation brain regions linked with the disease, wherein the activation of the brain regions comprises an increase of blood flow/neuronal activity in the brain regions of at last one of limbic system, basal ganglia and/or a midbrain of the patient; and
controlling via a control unit a flow of the generated pulses to the first electrode.

2. The method of claim 1, further comprising:
attaching a second active electrode to a second leg of the patient in the back of the knee area in an expected location of a peroneal nerve of the second leg;
generating electrical pulses by the pulse generator connected to the second active electrode;
stimulating by the second active electrode the peroneal nerve of the second leg and activating via the stimulation brain regions linked with the disease, wherein the activation of the brain regions comprises an increase of blood flow/neuronal activity in the brain regions of at least one of a limbic system, basal ganglia and/or a midbrain of the patient; and
controlling via a control unit a flow of the generated pulses to each of the first and second active electrode.

3. The method of claim 2, wherein stimulating of the first and the second peroneal nerve involves a simultaneous stimulation of the first and the second peroneal nerve.

4. The method of claim 2, wherein controlling involves setting voltage and; or current of the generated pulses to invoke a reflex movement of each of the first and the second leg of the patient.

5. The method of claim 4, wherein the reflexive movement is a periodical reflexive movement in a transversal plane of a foot belonging to the respective first and second leg of the patient.

6. The method of claim 2, further comprising:
detecting a reflex movement of each of the first and the second lot of the patient, wherein the reflexive movement is a response to the first and/or the second peroneal nerve stimulation.

7. The method of claim 6, the method further comprising:
monitoring the reflexive movement of each of the first and the second leg of the patient;
comparing the monitored reflex movement with a preset value of an expected reflex movement and based on the comparison determining whether the reflex movement is sufficient.

8. The method of claim 7, the method further comprising:
determining frequency of the periodical reflexive movement for each of the first and the second leg of the patient.

9. The method of claim 8, wherein controlling involves an automatic setting of the flow of the generated pulses to each of the first and the second active electrode depending on the determined frequency of the periodical reflexive movement of each of the first and the second leg of the patient.

10. The method of claim 8, wherein the automatic setting of the flow involves setting timing of generated pulses to each of the first and the second active electrode so that the periodical movements of the reflexive movement of the first and the second leg are synchronized.

11. The method of claim 2, wherein each of the active electrodes has an active conductive surface attached to the first or the second leg of the patient comprised between 0.0775 square inch (0.5 cm2) and 0.3100 square inch (2 cm2).

12. The method of claim 2, wherein each of the active electrodes has an active conductive surface attached to the first or the second leg of the patient less than 0.0775 square inch (0.5 cm2).

13. The method of claim 2, wherein each of the active electrodes has an active conductive surface attached to the first or the second leg of the patient comprised between 0.0155 square inch (0.1 cm2) and 0.0775 square inch (0.5 cm2).

14. The method of claim 1, wherein the grounding electrode is attached to patient's suprapubic or sacral area.

15. The method of claim 1, wherein the generated electrical pulses are electrical pulses with a frequency comprised between 2.5 Hz and 60 Hz and the electrical pulses have a pulse width comprised between 0.1 ms and 2.5 ms.

16. The method of claim 1, wherein the frequency of the electrical pulses is comprised between 0.5 Hz and 10 Hz or between 2.5 Hz and 10 Hz.

17. The method of claim 1, wherein the frequency of the electrical pulses is comprised between 2.5 Hz and 6 Hz.

18. The method of claim 1, wherein the voltage of the generated electrical pulses is less than 90 V and current of the electrical pulses is lower than 250 mA.

* * * * *